(12) United States Patent
Deladi et al.

(10) Patent No.: US 9,675,417 B2
(45) Date of Patent: Jun. 13, 2017

(54) SAFE ABLATION

(75) Inventors: Szabolcs Deladi, Eindhoven (NL); Nenad Mihajlovic, Eindhoven (NL); Ralph Kurt, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 363 days.

(21) Appl. No.: 13/003,022

(22) PCT Filed: Jul. 10, 2009

(86) PCT No.: PCT/IB2009/053003
§ 371 (c)(1),
(2), (4) Date: Jan. 7, 2011

(87) PCT Pub. No.: WO2010/007564
PCT Pub. Date: Jan. 21, 2010

(65) Prior Publication Data
US 2011/0118714 A1    May 19, 2011

(30) Foreign Application Priority Data
Jul. 15, 2008  (EP) .................................. 08160428

(51) Int. Cl.
*A61B 18/24* (2006.01)
*A61B 18/20* (2006.01)
(Continued)

(52) U.S. Cl.
CPC .......... *A61B 18/24* (2013.01); *A61B 18/1492* (2013.01); *A61B 18/28* (2013.01);
(Continued)

(58) Field of Classification Search
CPC ..... A61B 18/24; A61B 18/28; A61B 18/1492; A61B 2018/0023; A61B 2018/00666;
(Continued)

(56) References Cited

U.S. PATENT DOCUMENTS 4,307,942 A * 12/1981 Chahroudi .................... 359/241
5,785,703 A *  7/1998 Goodman et al. .............. 606/10
(Continued)

FOREIGN PATENT DOCUMENTS

CN           1961959       5/2007
WO       2008003642 A1    1/2008
WO    WO 2008/003642 A1 * 1/2008

OTHER PUBLICATIONS

Nathan Edward Reticker-Flynn, Design and Fabrication of Microfluidic Valves Using poly(N-isopropylacrylamide), Jun. 2008, Massachusetts Insititute of Technology,pp. 1-185.*
(Continued)

*Primary Examiner* — Gary Jackson
*Assistant Examiner* — Boniface N Nganga

(57) ABSTRACT

The present invention relates to a device comprising a supply unit (2) for supplying ablation energy to a material (4), and a stimuli-responsive substance (3') for controlling a level of the ablation energy deposited into the material (4). The device allows to limit a temperature of the material (4), so that risks associated to ablation at too high temperatures can be eliminated. The device may comprise at least one illumination unit (7) for illuminating the material (4), and at least one reception unit (8a, 8b) for receiving reflected light in order to obtain information about a state of the material (4). The obtained information can be used to regulate the supplied ablation energy.

9 Claims, 8 Drawing Sheets

(51) Int. Cl.
   *A61B 18/14* (2006.01)
   *A61B 18/28* (2006.01)
   *A61B 17/00* (2006.01)
   *A61B 18/00* (2006.01)

(52) U.S. Cl.
   CPC ............ *A61B 2017/00057* (2013.01); *A61B 2017/00084* (2013.01); *A61B 2018/00023* (2013.01); *A61B 2018/00666* (2013.01); *A61B 2018/00791* (2013.01)

(58) Field of Classification Search
   CPC .. A61B 2018/00791; A61B 2017/0057; A61B 2017/0084
   USPC .......................................................... 606/10
   See application file for complete search history.

(56) References Cited

U.S. PATENT DOCUMENTS

| | | |
|---|---|---|
| 6,172,795 B1 | 1/2001 | Carlson |
| 6,302,878 B1 | 10/2001 | Daikuzono |
| 6,508,813 B1 | 1/2003 | Altshuler |
| 7,135,034 B2* | 11/2006 | Friedman et al. .............. 607/88 |
| 8,784,407 B2 | 7/2014 | Spikker et al. |
| 2001/0056278 A1 | 12/2001 | Nield et al. |
| 2003/0165174 A1* | 9/2003 | Lawandy ........................ 372/53 |
| 2004/0223945 A1* | 11/2004 | Ohnishi et al. ............ 424/78.21 |
| 2004/0248326 A1* | 12/2004 | Ziaie et al. ....................... 438/1 |
| 2005/0135772 A1 | 6/2005 | Nield et al. |
| 2007/0005052 A1 | 1/2007 | Kampa |
| 2007/0224169 A1 | 9/2007 | Sliwa, Jr. et al. |
| 2007/0225564 A1 | 9/2007 | Couvillon, Jr. et al. |
| 2009/0053276 A1* | 2/2009 | Richard ........................ 424/422 |
| 2011/0118714 A1 | 5/2011 | Deladi et al. |

OTHER PUBLICATIONS

A.D Semenov, G.N Gol'tsman, I.G. Gogidze, A.V. Sergeev, E.M Gershenzon et al., Subnanosecond photoresponse of a YBaCuO thin film to infrared and visible radiation by quasiparticle induced suppression of superconductivity, Appl. Phys. Lett. 60, p. 903 (1992); doi: 10.1063/1.106500.*

* cited by examiner

SAFE ABLATION

FIELD OF THE INVENTION

The present invention generally relates to a device and a method enabling a safe ablation of material by thermally treating the same.

BACKGROUND OF THE INVENTION

A thermal therapy has been used for treating various diseases. For example, an interventional treatment such as a minimally-invasive treatment of cardiac arrhythmias (e.g. an atrial fibrillation (AF)) and other diseases is possible. In such treatment, cardiac tissue is denaturised by a thermal therapy. Heated muscle cells in cardiac tissue are denaturated and lose their biological function, which can be measured by an increase in the tissue impedance. Furthermore, in oncology, cancer cells are heated up in order to destroy their biological function. Different kinds of tissue and other material can also be thermally treated, not only for therapy applications but also for other purposes.

In the minimally-invasive treatment of cardiac arrhythmias and other diseases, ablation catheters are the most commonly-used therapy tools. However, catheter ablation procedures still have significant drawbacks, and research and development continue in this active field. One major drawback is in controlling the ablation settings during treatment. Currently, the therapists rely on their own expertise to guess the optimal parameters for ablation, such as power, temperature, and duration. These settings vary largely, due to sizable intra-patient differences of e.g. thickness of the local heart wall, perfusion, blood pressure and velocity, heart rhythm, etc.

A thermal therapy is mainly performed by using radio frequency (RF) catheters (in heart tissue ablation), but laser light and high intensity focused ultrasound (HIFU) are used as alternative energy sources. The main benefit of using laser light is a high level of miniaturization, since laser energy can be transported through a very thin fiber. Furthermore, such intervention can be performed without any adaptations in combination with magnetic resonance imaging (MRI), since fibers are MR safe and compatible.

However, when a laser source is used for a thermal therapy, an overheating may occur and there are limited possibilities for control of the thermal process. A major risk related to a catheter therapy is attributed to the overheating of the ablation site. In the case of overheating, either rupturing of the tissue at the ablation or treatment site (releasing potentially life-threatening particles into the blood stream) or damage to neighboring organs and tissues is inflicted. In the case that other organs are affected, fistulas can develop. Such fistulas are often life-threatening. For example, a fistula in the esophagus has a mortality rate of roughly 75%.

An overheating occurs at a point where laser energy is deposited into the tissue. In order to prevent such overheating, an irrigation can be performed, or the temperature of the tissue can be measured. However, if an irrigation is performed, at least one irrigation tube needs to be added to the fiber transporting the laser energy. Furthermore, if an external irrigation is performed, then, during the thermal therapy, additional liquid is pumped into a treated patient, which limits the time of the procedure, but can also cause some complications and side effects. On the other hand, the temperature cannot be measured at the point where an overheating first occurs. If any sensor is placed at that point, then laser light directly heats up the sensor. Therefore, the sensor mainly measures temperature due to light absorption of the sensor, while it should measure the temperature of the heated tissue.

SUMMARY OF THE INVENTION

It is an object of the present invention to alleviate at least some of the above drawbacks.

This object can be achieved devices and methods as described and claimed herein.

Accordingly, in a first aspect of the present invention, a device is presented. The device can comprise a supply unit configured to supply ablation energy to a material, and a container comprising a stimuli-responsive substance. The stimuli-responsive substance may be configured to change its state from a first state to a second state if a temperature of the material increases above an upper threshold temperature due to the ablation energy, so that the temperature of the material does not increase above a temperature limit. This enables an elimination of the risk of an accidental overheating, due to an autonomous temperature-correlated energy dosing at an ablation site. A range of temperatures of a thermal treatment can be limited to a certain threshold. In this way, it may be ensured that a treated material does not get exposed to an extremely high energy dose. Thus, for example a carbonization or damage of collateral organs (e.g. the esophagus in an atrial fibrillation treatment) may be prevented. Hence, a safe ablation can be performed.

In a second aspect of the present invention, the stimuli-responsive substance may be configured to change its state back from the second state to the first state if the temperature of the material decreases below a lower threshold temperature. Hence, a reversible change of state is enabled. This allows repeated changes to a state where the temperature of the material is limited and back.

In a third aspect of the present invention, the stimuli-responsive substance may be a temperature-sensitive gel. Thus, it can change its properties in dependence on the temperature of the material in order to prevent an overheating of the same.

In a fourth aspect of the present invention, the supply unit may be configured to supply the ablation energy through the stimuli-responsive substance, and the stimuli-responsive substance can be configured to change its optical properties from being transparent to being scattering and/or absorbing if the temperature of the material increases above the upper threshold temperature. Hence, the stimuli-responsive substance may prevent that the ablation energy reaches the material once the temperature of the material is above the upper threshold temperature. Thus, the temperature of the material can decrease as the material is not heated up any longer.

In a fifth aspect of the present invention, the device may comprise a cooling system configured to cool the device, wherein the stimuli-responsive substance can be configured to change its geometrical properties in order to control the cooling system. The cooling system may be enabled or opened if the temperature of the material increases above the upper threshold temperature. In this way, an active cooling can be achieved, and the temperature of the material may be reduced. If the temperature of the material decreases below a lower threshold temperature, the cooling system can be disabled or closed. Thus, it is possible to keep the temperature of the material in a certain range.

In a sixth aspect of the present invention, in the device according to the fifth aspect, the cooling system may comprise at least one inflow pipe and at least one outflow pipe, and the container can comprise at least one flexible portion configured to disable a connection between the at least one inflow pipe and the at least one outflow pipe at least partially if the temperature of the material is equal to or below the upper threshold temperature and to enable the connection if the temperature of the material increases above the upper threshold temperature. If the temperature of the material is equal to or below the upper threshold temperature, the at least one flexible portion may be pushed to disable the connection between the inflow and outflow pipes at least partially. Thus, it can be prevented that cooling fluid flows through the cooling system, or only a reduced amount of the cooling fluid may be allowed to flow. If the temperature of the material increases above the upper threshold temperature, the stimuli-responsive substance can shrink. Consequently, the at least one flexible portion may retract and enable the connection between the inflow and outflow pipes, letting the cooling fluid flow through the cooling system. Hence, the temperature of the device and consequently that of the material can be reduced.

In a seventh aspect of the present invention, in the device according to the fifth aspect, the cooling system can comprise at least one portion configured to extend around the supply unit. Thus, cooling fluid may flow around the supply unit, without crossing a path of the ablation energy. Hence, it is not necessary that the cooling fluid is transparent to the ablation energy.

In an eighth aspect of the present invention, the supply unit can be a fiber and the ablation energy may be laser energy. In this way, a high level of miniaturization can be achieved, since the laser energy can be transported to an ablation site through a very thin fiber.

In a ninth aspect of the present invention, the device may comprise an irrigation system configured to supply and/or drain a fluid, wherein the stimuli-responsive substance can be configured to change its geometrical properties in order to control the irrigation system. The irrigation system may be used to perform an irrigation in order to prevent an overheating or for other purposes. By controlling it, an amount of irrigation fluid used during an ablation procedure does not become very significant. Thus, an irrigation fluid overload causing side effects can be avoided.

In a tenth aspect of the present invention, the device may comprise at least one illumination unit configured to illuminate the material, and at least one reception unit configured to receive reflected light in order to obtain information about a state of the material. Thus, an ablation procedure may be controlled by means of the obtained information. Further, a therapist or other operator of the ablation procedure can be provided with information about the same.

In an eleventh aspect of the present invention, in the device according to the tenth aspect, a first reception unit of the at least one reception unit may be configured to receive reflected light passing through the stimuli-responsive substance, and a second reception unit of the at least one reception unit can be configured to receive reflected light not passing through the stimuli-responsive substance. Thus, a direct feedback on a behavior of the stimuli-responsive substance and a development of an ablation site may be provided at the same time, while protecting the material from being overheated.

In a twelfth aspect of the present invention, in the device according to the eleventh aspect, the at least one illumination unit can be configured to illuminate the material through the stimuli-responsive substance. Thus, illumination light as well as reflected light received by the first reception unit may pass through the stimuli-responsive substance. Hence, an improved feedback on the behavior of the stimuli-responsive substance is possible.

In a thirteenth aspect of the present invention, the device can be a catheter or a needle. Thus, a catheter or an intelligent needle enabling an elimination of the risk of an accidental overheating and, therefore, a safe ablation is feasible.

In a fourteenth aspect of the present invention, a system is presented. The system may comprise a device according to the tenth aspect, at least one energy source configured to supply the ablation energy to the device, and a control unit configured to regulate the at least one energy source based on the obtained information. Thus, information on a status of a material treated by the device (e.g. information on size, quality, speed of lesion formation, etc.) can be gained and used to determine a time and power of the supplied ablation energy.

In a fifteenth aspect of the present invention, a method is presented. The method may comprise supplying ablation energy to a material, and changing a state of a stimuli-responsive substance from a first state to a second state if a temperature of the material increases above an upper threshold temperature due to the ablation energy, so that the temperature of the material does not increase above a temperature limit. It enables an elimination of the risk of an accidental overheating, due to an autonomous temperature-correlated energy dosing at an ablation site. A range of temperatures of a thermal treatment can be limited to a certain threshold. In this way, it may be ensured that a treated material does not get exposed to an extremely high energy dose. Thus, for example a carbonization or damage of collateral organs (e.g. the esophagus in an atrial fibrillation treatment) may be prevented. Hence, a safe ablation can be performed.

Further advantageous modifications are defined in the dependent claims.

BRIEF DESCRIPTION OF THE DRAWINGS

These and other aspects of the present invention will be apparent from and elucidated by embodiments described hereinafter, by way of example, with reference to the accompanying drawings, in which.

DETAILED DESCRIPTION OF EMBODIMENTS

Stimuli-responsive substances (e.g. hydrogels) are capable of changing e.g. shape, size (volume) or optical properties in response to external stimuli such as e.g. the temperature. In the following, various examples of an incorporation of such substances into a tip of a device in order to enable a temperature-correlated energy dosing at an ablation or treatment site are presented. In particular, examples of using stimuli-responsive substances that can change their optical properties (e.g. scattering and/or absorbing capabilities) and/or geometrical properties (e.g. volume and/or shape) at temperature variation are discussed. These examples are to be considered illustrative or exemplary and not restrictive.

Figure 1:
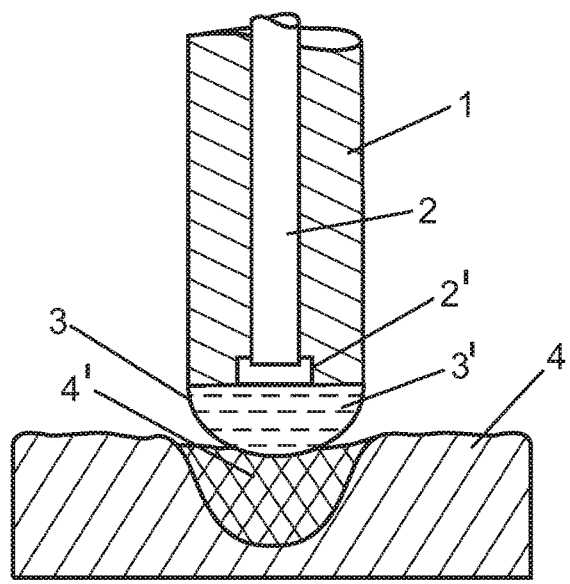
FIG. 1 shows a schematic diagram illustrating an exemplary device according to a first embodiment.

FIG. 1 shows a schematic diagram illustrating an exemplary device according to a first embodiment. It depicts a schematic cross section of a catheter that may be applied to thermally treat material. More specifically, it depicts a cross section of the distal end of the catheter, i.e. the catheter tip.

In the following, a medical application of the catheter is described. However, the below description is to be considered illustrative or exemplary and not restrictive. Other application areas are possible, such as e.g. a thermal treatment of some machine or other arrangement in order to ablate a certain portion of material forming part of the same. For example, a part made of metal or alloy and positioned adjacent to a part made of plastic can be treated, wherein a destruction of the more temperature-sensitive part made of plastic may be avoided by limiting the applied energy dose.

FIG. 1 shows that the catheter tip is rounded off, i.e. has a curved border in the depicted schematic cross section. However, other variants are feasible. For example, the catheter tip may have straight and curved portions or just a straight portion as illustrated in other figures.

The catheter can comprise a catheter housing 1, a supply unit 2 such as e.g. an (optical) fiber or ablation fiber, an (optional) element 2' covering the distal end of the supply unit 2, and a container 3 comprising a stimuli-responsive material or substance 3'. It may be used to thermally treat a target material 4, wherein this treatment may be applied to an area or site 4' at the material 4 in order to ablate the same. The ablation or treatment site 4' can be considered to be some kind of lesion in case of treating tissue.

In general, everything between the distal end of the supply unit 2 and the treatment site 4' should be transparent to ablation energy supplied by the supply unit 2. For example, in case that laser energy (light) is supplied by the supply unit 2, everything between the distal end of the supply unit 2 and the treatment site 4' should be optically transparent, so that the laser energy can pass through.

If the distal end of the supply unit 2 is too far away from the treatment area 4', then a lot of ablation laser light may be absorbed into a transparent part of the catheter. This can result in an increase of the temperature of the tip of the catheter, which is not wanted. On the other hand, if the end of the supply unit 2 is in contact with the material 4, then the breadth of the treatment area 4' is very small (in the order of the diameter of the core of the supply unit 2 such as a fiber). Furthermore, a lot of optical power is then deposited through a very small surface. Therefore, a local overheating may occur. An overheating can result in a local damage to the material 4. For example, if the material 4 is a human or animal tissue, a local tissue carbonization and even vaporization (small explosions) may occur in a very short time. Vaporization and carbonization are unwanted and can even damage the supply unit 2.

Thus, there is an optimal distance between the distal end of the supply unit 2 and the treatment area 4' in such a way that losses due to a light absorption into transparent material are low, and the size of the treatment area 4' is large enough. The optimal distance can depend on a respective application. For example, it may vary between a few millimeters and several centimeters.

The space between the distal end of the supply unit 2 and the treatment area 4' can be filled in different ways. While FIG. 1 shows an arrangement in which the distal end of the supply unit 2 is covered by an element 2' having a u-shaped cross section, several variants are feasible. For example, the element 2' may be a slab of transparent material or have another shape. Further, the supply unit 2 can extend up to the border of the container 3. Moreover, the container 3 may comprise some kind of recess, and the supply unit 2 can extend into such recess. The supply unit 2 might even extend into the stimuli-responsive substance 3', wherein in practice variants with a closed container 3 might be preferred. In addition, a container filled with an irrigation or cooling liquid used for cooling purposes may be located between the distal end of the supply unit 2 and the treatment area 4'. Thus, the space between these elements can comprise a lumen filled with an irrigation or cooling liquid used for cooling and/or with additional transparent material that may be part of the construction of the catheter.

An ablation may be performed with the catheter tip contacting or not contacting the material 4, during which ablation energy such as e.g. laser energy supplied by the supply unit 2 and passing through the element 2' and the container 3 can be deposited into the material 4. In case that the material 4 is some kind of tissue, a heating and denaturation of proteins may be caused. Once the temperature of the material 4 has reached a certain (upper) threshold temperature, the stimuli-responsive substance 3' can change its optical properties from being transparent to becoming scattering and/or absorbing. A level of energy reaching the material 4 may decrease subsequently. Therefore, the temperature of the material 4 can decrease accordingly. Once the temperature of the targeted material 4 is low enough, the stimuli-responsive substance 3' may change its optical properties from being scattering and/or absorbing to being transparent. Thus, the level of energy deposited into the material 4 during the ablation process can increase again. Hence, a state of the stimuli-responsive substance 3' can reversibly change.

As described above, the stimuli-responsive substance 3' may change its state from a first state to a second state if the temperature of the material 4 increases above an upper threshold temperature due to the ablation energy, so that the temperature of the material does not increase above a temperature limit of e.g. 70° C. and detrimental effects due to an overheating are prevented. On the other hand, the stimuli-responsive substance 3' can change its state back from the second state to the first state if the temperature of the material 4 decreases below a lower threshold temperature that may be identical with the upper threshold temperature or differ from the same. Thus, the temperature of the material 4 does not decrease below a further temperature limit.

In this manner, the temperature of the material 4 can be kept in a certain interval, without the risk of exceeding a temperature threshold or limit. Thus, detrimental effects resulting from an overheating may be avoided. For example, due to an overheating of tissue (above 70 to 75° C.) particles can be released in the blood stream, having life-threatening consequences. This may be prevented by the described limitation of the level of energy deposited into the tissue, i.e. by a limitation of the applied energy dose.

As described above, a safe ablation catheter based on a stimuli-responsive substance can be provided. The stimuli-responsive substance changing its optical properties from being transparent to being scattering and/or absorbing may regulate a level of energy deposited into a target material. In this way, the temperature of the material can be regulated. Thus, an overheating of the material may be prevented.

Figure 2:
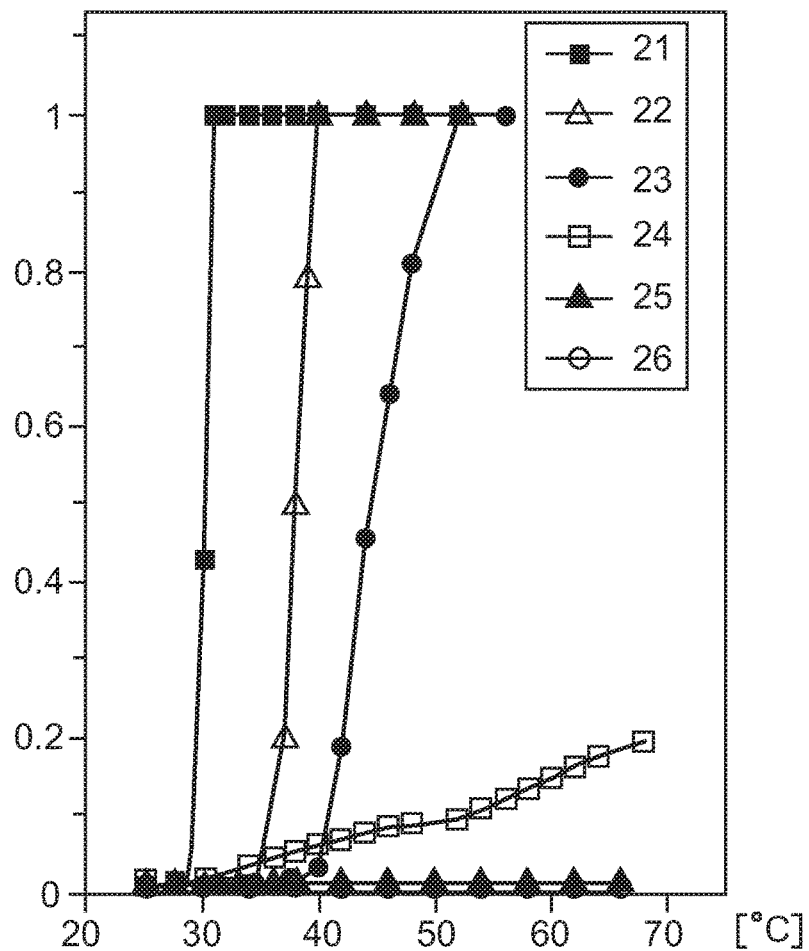
FIG. 2 shows a schematic diagram illustrating an absorbency of an exemplary stimuli-responsive substance versus the temperature for various pH-values of the stimuli-responsive substance.

A variety of substances may be used as the stimuli-responsive substance 3'. Some of these substances undergo very abrupt changes in optical properties in response to external stimuli such as e.g. the temperature. This effect is known as lower critical solution temperature (LCST). For example, some hydrogels undergo a very sharp transition when increasing the temperature and change from an optically transparent material into a scattering material. FIG. 2 illustrates such an example, where the temperature threshold can be varied by changing the pH-value of the stimuli-responsive substance.

FIG. 2 shows a schematic diagram illustrating an absorbency of an exemplary stimuli-responsive substance versus the temperature for various pH-values of the stimuli-responsive substance. On the horizontal axis the temperature in ° C. is indicated, and on the vertical axis the absorbency of a P(NIP-co-AAc-20) solution at a laser light wavelength of 450 nm is indicated as a function of the pH-value. Reference values 21 to 26 denote curves for pH-values of 2.2, 3.9, 4.2, 4.5, 6.4 and 9.2, respectively. As illustrated in FIG. 2, the lower the pH-value is, the earlier (i.e. at lower temperature) and steeper the respective curve ascends. For example, the curve 21 for a pH-value of 2.2 increases very steeply if the temperature approaches about 30° C., the curve 23 for a pH-value of 4.2 increases less steeply if the temperature approaches about 40° C., and the curve 26 for a pH-value of 9.2 does not substantially increase at all regardless of the temperature.

The particular solution used to generate the absorbency diagram shown in FIG. 2 is one example of a stimuli-responsive substance that may not be directly relevant to a laser ablation process. However, similar stimuli-responsive substances in the interval of wavelengths (488-532 nm, 800-1100 nm) used for ablation can exist or may be developed. A practical example of a stimuli-responsive substance is a temperature-sensitive hydrogel with a reaction mixture consisting of 25 weight-weight percentage (wt %) deionized water, 25 wt % methanol, 48.9 wt % NIPAAm+0.1 wt % diethyleneglycoldiacrylate+1 wt % IRG 2959 photo-initiator, which is polymerized by applying ultraviolet (UV) radiation (100 mW/cm$^2$) for about 90 seconds. Further examples are described in the following.

For instance, temperature-responsive materials undergoing a phase transition (including melting, crystalline-amorphous transition, LCST or other transitions) may be used as stimuli-responsive substances. For example, (hydrophilic) polymers, copolymers or hydrogels exhibiting a LCST may be used as stimuli-responsive substances. These polymers, copolymers or hydrogels switch from a transparent to a scattering state above the LCST. Non-limitative examples of temperature-responsive polymers include polymers, copolymers or hydrogels based on one or more of the following monomers: N-substituted acrylamides (e.g. N-alkylacrylamides, as N-isopropylacrylamide, di(m)ethylacrylamide, carboxyisopropylacrylamide, hydroxymethylpropylmethacrylamide, etc.), acryloylalkylpiperazine and N-vinylcaprolactam as well as copolymers thereof with hydrophilic monomers such as but not limited to hydroxyethyl(meth)acrylate, (meth)acrylic acid, acrylamide, polyethyleneglycol(meth)acrylate, N-vinylpyrrolidone, dimethylaminopropylmethacrylamide, dimethylaminoethylacrylate, N-hydroxymethylacrylamide or mixtures thereof, and/or copolymerized with hydrophobic monomers such as but not limited to (iso)butyl(meth)acrylate, methylmethacrylate, isobornyl(meth)acrylate, glycidyl methacrylate or mixtures thereof. Examples of useful polymers are poly(N-isopropylacrylamide) (LCST=32° C.), poly(N,N'-diethyl-acrylamide) (LCST=25 to 35° C.) and poly(-N-acryloyl-N'-alkylpiperazine) (LCST=37° C.). The N-substituted acrylamides may be copolymerized with for instance oxyethylene, trimethylol-propane distearate, e-caprolactone and mixtures thereof among others. The skilled person is able to design monomer mixtures, in terms of monomer selection and proportions of monomers, that are able to tailor a desirable LCST at will, e.g. within a range from about 30° C. to about 70° C.

Temperature-responsive polymer hydrogels may be made for instance by mixing one or more of the above-listed monomers with an effective amount of one or more known crosslinking agents in the presence of an aqueous medium (e.g. water or a water/methanol mixture), and bringing the resulting mixture to a temperature range where partial or complete polymerization and crosslinking occurs. As known to the skilled person, by an appropriate selection of the monomers, the crosslinking agent type and amount, and/or the polymerization conditions (temperature and time), the LCST and the viscosity of the resulting polymer hydrogel can be tailored at will. Suitable but non-limiting examples of monomer mixtures comprise N-isopropyl acrylamide-polyethyleneglycol monoacrylate mixtures, wherein the polyethyleneglycol monoacrylate amounts from about 2% by mole to about 20% by mole of the monomer mixture. Other suitable comonomers include, but are not limited to, dimethylaminopropyl methacrylamide, N-hydroxymethylacrylamide, glycidyl methacrylate and the like. Suitable examples of crosslinking agents for the aqueous phase (co)polymerization of N-substituted acrylamides include, but are not limited to, N-methyl-bisacrylamide, diethyleneglycol diacrylate and the like. The molar ratio of monomer(s) and crosslinking agent(s) may suitably be in the range between 1:25 and 1:1000. Furthermore, an initiator (either a photo-initiator or a thermal initiator) can be added in order to initiate polymerization, e.g. in a 1 to 5 weight % ratio with respect to the monomer(s). The one or more monomers may be mixed with an aqueous solvent medium ($H_2O$ or a $H_2O$/methanol mixture), typically in an amount between about 50 and about 90% by weight of the total mixture, and the mixture can subsequently be (co)polymerized until a hydrogel is formed. Hydrogel materials that may be used can comprise ≥50% by weight water and/or solvent, e.g. ≥70% by weight or ≥90% by weight, wherein solvents may include organic solvents, e.g. organic polar solvents, and alkanols such as ethanol, methanol and/or (iso-)propanol.

A hydrogel material can comprise a material selected out of the group comprising poly(meth)acrylic materials, silica gel materials, substituted vinyl materials or mixtures thereof. Further, the hydrogel material may comprise a poly(meth) acrylic material obtained from a polymerization of at least one (meth)acrylic monomer and at least one polyfunctional (meth)acrylic monomer. The (meth)acrylic monomer can be selected from the group consisting of (meth)acrylamide, (meth)acrylic acid, hydroxyethyl(meth)acrylate, ethoxyethoxyethyl(meth)acrylate or mixtures thereof among others. The polyfunctional (meth)acrylic monomer may be a bis-(meth)acrylic and/or a tri-(meth)acrylic and/or a tetra-(meth)acrylic and/or a penta-(meth)acrylic monomer. The polyfunctional (meth)acrylic monomer can be selected from the group consisting of bis(meth)acrylamide, tripropyleneglycol di(meth)acrylates, pentaerythritol tri(meth)acrylate, polyethyleneglycol di(meth)acrylate, ethoxylated bisphenol-A-di(meth)acrylate, hexanediol di(meth)acrylate or mixtures thereof in any suitable proportions, among others.

The hydrogel material may comprise an anionic poly (meth)acrylic material, selected e.g. from the group consisting of (meth)acrylic acids, arylsulfonic acids, especially styrenesulfonic acid, itaconic acid, crotonic acid, sulfonamides or mixtures thereof, and/or a cationic poly(meth)acrylic material, selected e.g. from the group consisting of vinyl pyridine, vinyl imidazole, amino ethyl (meth)acrylates or mixtures thereof, copolymerized with at least one monomer selected from the group of neutral monomers, selected e.g. from the group consisting of vinyl acetate, hydroxyethyl (meth)acrylate(meth)acrylamide, ethoxyethoxyethyl (meth) acrylate or mixtures thereof in any suitable proportions, among others.

The hydrogel material can comprise a silica gel material. Further, it may comprise a substituted vinyl material, e.g. vinylcaprolactam and/or substituted vinylcaprolactam.

Stimuli-responsive substances can comprise one or more thermo-responsive hydrogel materials based on monomers selected from the group consisting of N-isopropylamide, diethylacrylamide, carboxyisopropylacrylamide, hydroxymethylpropylmethacrylamide, acryloylalkylpiperazine and copolymers thereof with monomers selected from the group of the hydrophilic monomers, this group comprising hydroxyethyl(meth)acrylate, (meth)acrylic acid, acrylamide, polyethyleneglycol(meth)acrylate or mixtures thereof, and/or copolymerized with monomers selected from the group of hydrophobic monomers, comprising (iso)butyl(meth)acrylate, methylmethacrylate, isobornyl(meth)acrylate or mixtures thereof in any suitable proportions. These copolymers are known to be thermo-responsive. Therefore, they may be of use as stimuli-responsive substances.

Figure 3:
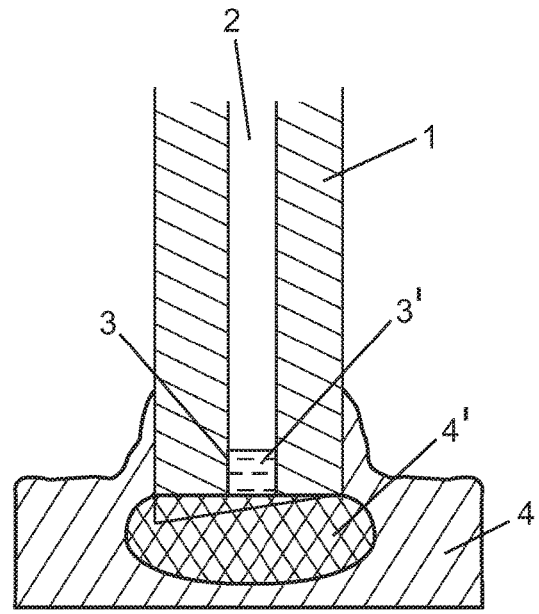
FIG. 3 shows a schematic diagram illustrating an exemplary device according to a second embodiment.

FIG. 3 shows a schematic diagram illustrating an exemplary device according to a second embodiment. It depicts a schematic cross section of a needle that may be applied to thermally treat material. More specifically, it depicts a cross section of the distal end of the needle, i.e. the needle tip.

The needle can comprise a needle housing 1, a supply unit 2 such as e.g. an (optical) fiber or ablation fiber, an (optional) element 2' covering the distal end of the supply unit 2, and a container 3 comprising a stimuli-responsive material or substance 3', wherein the element 2' is not shown in FIG. 3. These components as well as a target material 4 and an area or site 4' at the material 4 may be identical with or similar to the elements denoted by the same reference numerals as shown in FIG. 1 and described in connection with the first embodiment. Therefore, they are not described in detail again.

The needle according to the second embodiment can have an open tip suitable to puncture the material 4 as shown in FIG. 3. The needle may be used to thermally treat the material 4 while its tip is inserted into the same, i.e. a puncture of the material 4 is performed. The treatment can be applied to the site 4' at the material 4 in order to ablate the same. As shown in FIG. 3, in this case the ablation or treatment site 4' may not be placed at the surface of the material 4 but rather located inside of the material 4.

The needle according to the second embodiment enables to perform an ablation in the same manner as described in connection with the first embodiment. Thus, a level of energy deposited into the material 4 can be regulated. In this way, an overheating of the material 4 and detrimental effects resulting from such overheating may be avoided. Hence, a safe ablation needle based on a stimuli-responsive substance can be provided. The needle may be called an intelligent needle.

Figure 4A:
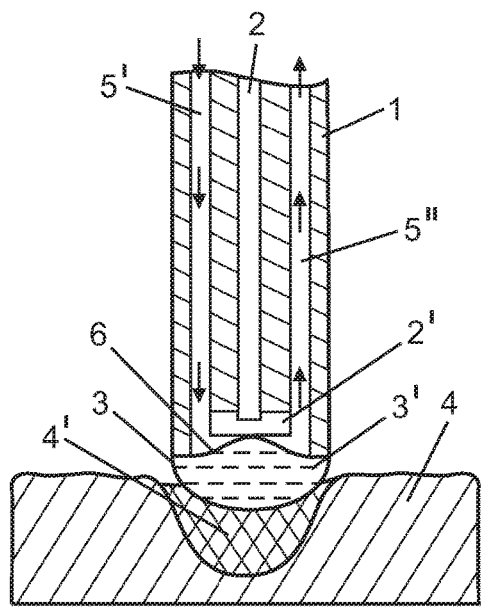
FIGS. 4(a) and 4(b) show schematic diagrams illustrating an exemplary device according to a third embodiment.
Figure 4B:
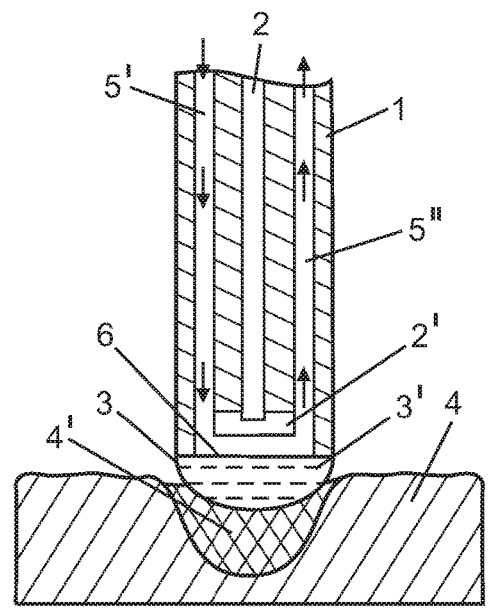

While FIG. 3 shows an arrangement where the ablation energy such as e.g. laser energy (light) supplied by the supply unit 2 passes only through the container 3 comprising the stimuli-responsive substance 3', other variants as described in connection with the first embodiment are feasible. For example, while no element 2' is shown in FIG. 3, such element can be present. Further, the same considerations with respect to the distance between the distal end of the supply unit 2 and the treatment area 4' as for the first embodiment apply. FIGS. 4(a) and 4(b) show schematic diagrams illustrating an exemplary device according to a third embodiment. They depict schematic cross sections of a catheter that may be applied to thermally treat material. More specifically, they depict cross sections of the distal end of the catheter, i.e. the catheter tip.

The catheter can comprise a catheter housing 1, a supply unit 2 such as e.g. an (optical) fiber or ablation fiber, an (optional) element 2' covering the distal end of the supply unit 2, and a container 3 comprising a stimuli-responsive material or substance 3'. These components as well as a target material 4 and an area or site 4' at the material 4 may be identical with or similar to the elements denoted by the same reference numerals as shown in FIG. 1 and described in connection with the first embodiment, except for the stimuli-responsive substance 3'. Therefore, they are not described in detail again.

In addition to the above components, the catheter according to the third embodiment can comprise at least one tour or inflow pipe 5' and at least one return or outflow pipe 5" forming a cooling system for cooling the catheter tip and in turn the material 4. Further, the container 3 may comprise at least one flexible portion 6 such as e.g. a flexible wall. These additional components enable an active cooling control of the catheter tip by means of the stimuli-responsive substance 3' as described in more detail below.

Stimuli-responsive substances that are capable of changing their geometrical properties (e.g. volume and/or shape) in response to external stimuli can be employed in the catheter according to the third embodiment. For example, a temperature-sensitive hydrogel material (e.g. poly(N-isopropylacrylamide) (PNiPAAm)) capable of swelling/shrinking in dependence on the temperature may be used as the stimuli-responsive substance 3'. Such material may shrink if the temperature increases. This effect can be used to actuate mechanical parts such as the at least one flexible portion 6 of the container 3.

The catheter according to the third embodiment enables to perform an ablation in the same manner as described in connection with the first embodiment. When the temperature of the material 4 is below a certain (upper) threshold temperature, the stimuli-responsive substance 3' may occupy a larger volume. Thus, it can push the at least one flexible portion 6 of the container 3 that subsequently obstructs or partially obstructs the flow of cooling fluid in the cooling system. That is, the least one flexible portion 6 may be pushed to disable a connection between the at least one inflow pipe 5' and the at least one outflow pipe 5" at least partially as long as the temperature of the material 4 is equal to or below an upper threshold temperature. Thus, it can be prevented that cooling fluid flows through the cooling system, or only a reduced amount of the cooling fluid may be allowed to flow. FIG. 4(*a*) illustrates the state where the temperature of the material 4 is below the threshold temperature and, therefore, the cooling system is closed or at least partially closed.

Once the temperature of the material 4 increases above the threshold temperature, the stimuli-responsive substance 3' can shrink. As a consequence, the at least one flexible portion 6 may not be pushed and retract, letting the cooling fluid or an increased amount of the cooling fluid flow through the cooling system. That is, if the temperature of the material 4 increases above the upper threshold temperature, the connection between the at least one inflow pipe 5' and the at least one outflow pipe 5" can be enabled. As a result, the temperature of the catheter tip and consequently that of the material 4 can be reduced. FIG. 4(*b*) illustrates the state where the temperature of the material 4 is above the threshold temperature and, therefore, the cooling system is open.

As described above, the stimuli-responsive substance 3' may change its state from a first state to a second state if the temperature of the material 4 increases above the upper threshold temperature due to the ablation energy, so that the temperature of the material 4 does not increase above a temperature limit of e.g. 70° C. and detrimental effects due to an overheating are prevented. On the other hand, the stimuli-responsive substance 3' can change its state back from the second state to the first state if the temperature of the material 4 decreases below a lower threshold temperature that may be identical with the upper threshold temperature or differ from the same. Thus, the temperature of the material 4 does not decrease below a further temperature limit.

In this manner, the temperature of the material 4 can be kept in a certain interval, without the risk of exceeding a temperature threshold or limit. Thus, detrimental effects resulting from an overheating may be avoided.

According to the third embodiment, a path from the distal end of the supply unit 2 to the ablation or treatment site 4' intersects the cooling system. Further, this path intersects the stimuli-responsive substance 3'. The path should be free for the ablation energy, so that the ablation energy can reach the treatment site 4'. If e.g. laser energy (light) is supplied by the supply unit 2, the path is an optical path. In this case, the cooling fluid and the stimuli-responsive substance 3' should be optically transparent, so that the laser energy can pass through.

While only a single inflow pipe 5' and a single outflow pipe 5" are shown in FIGS. 4(*a*) and 4(*b*), multiple inflow pipes and/or multiple outflow pipes may be present. Further, there can be a plurality of containers 3 respectively comprising a stimuli-responsive substance 3' capable of changing its geometrical properties and at least one flexible portion 6 pushed by the stimuli-responsive substance 3'.

While FIGS. 4(*a*) and 4(*b*) show a specific arrangement, other variants as described in connection with e.g. the first embodiment are feasible. Further, the same considerations with respect to the distance between the distal end of the supply unit 2 and the treatment area 4' as for the first embodiment apply.

As described above, a safe ablation catheter based on a catheter tip cooling system can be provided. The stimuli-responsive substance 3' may change its geometrical properties in order to control the cooling system. In this way, the temperature of the material 4 can be regulated by cooling it with the catheter tip in turn cooled by the cooling system. Thus, an overheating of the material 4 and detrimental effects resulting from such overheating may be prevented.

Figure 5:
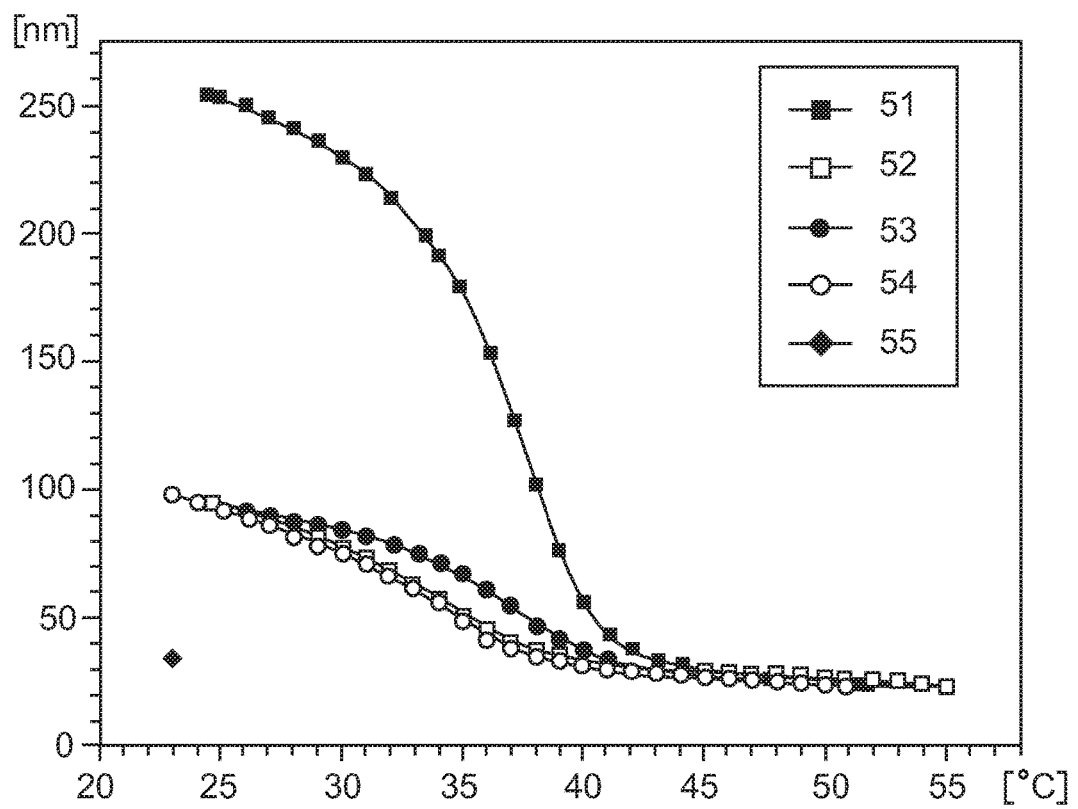
FIG. 5 shows a schematic diagram illustrating a thickness of a layer of an exemplary stimuli-responsive substance versus the temperature during first and second heating/cooling cycles.

FIG. 5 shows a schematic diagram illustrating a thickness of a layer of an exemplary stimuli-responsive substance versus the temperature during first and second heating/cooling cycles. On the horizontal axis the temperature T in ° C. is indicated, and on the vertical axis a layer thickness d in nm is indicated. The depicted curves have been obtained for a PNiPAAm film or layer. Reference values 51 to 54 denote curves for a first heating cycle, a first cooling cycle, a second heating cycle and a second cooling cycle, respectively. A reference value 55 denotes a state before swelling. As illustrated in FIG. 5, the layer thickness decreases from above 250 nm to below 30 nm in the first heating cycle and subsequently increases to above 90 nm in the first cooling cycle. Then, the layer thickness decreases from above 90 nm to below 30 nm in the second heating cycle and subsequently again increases to above 90 nm in the second cooling cycle. With increasing temperature a respective shrinking can be observed. The layer thickness varies in a range between 20 nm and 100 nm after the first heating cycle. Thus, a cooling system can be continuously controlled by means of a layer made of PNiPAAm or another stimuli-responsive substance capable of changing its geometrical properties in response to external stimuli such as e.g. the temperature.

Figures 6A, 6B:
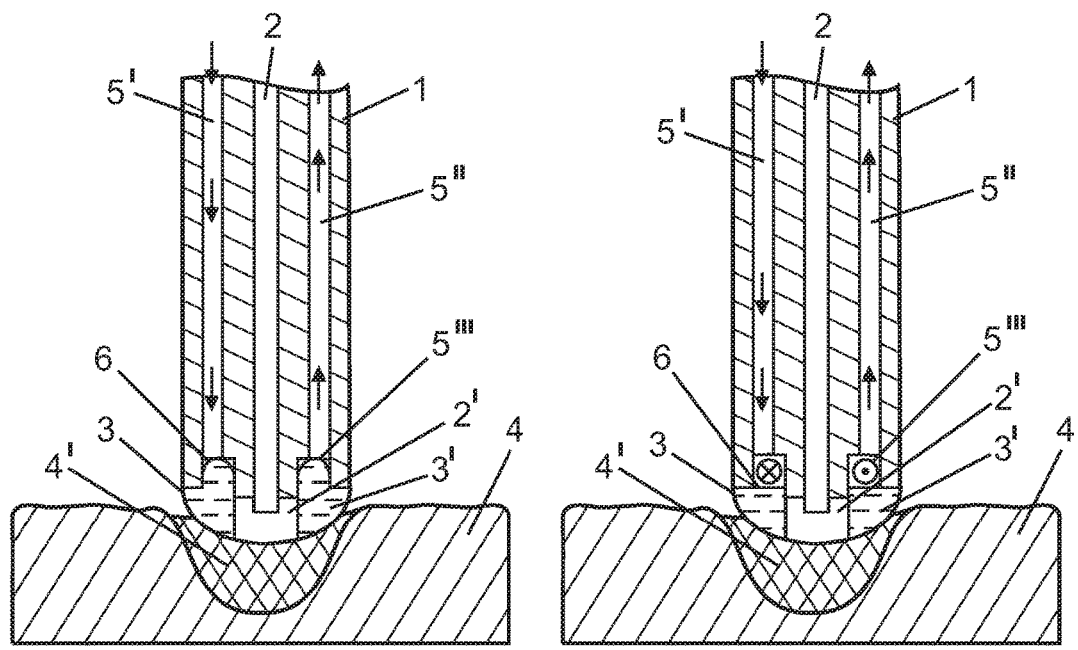
FIGS. 6(a) and 6(b) show schematic diagrams illustrating an exemplary device according to a fourth embodiment.

FIGS. 6(*a*) and 6(*b*) show schematic diagrams illustrating an exemplary device according to a fourth embodiment. They depict schematic cross sections of a catheter that may be applied to thermally treat material. More specifically, they depict cross sections of the distal end of the catheter, i.e. the catheter tip.

The catheter can comprise a catheter housing 1, a supply unit 2 such as e.g. an (optical) fiber or ablation fiber, an (optional) element 2' covering the distal end of the supply unit 2, and a container 3 comprising a stimuli-responsive material or substance 3'. These components as well as a target material 4 and an area or site 4' at the material 4 may be identical with or similar to the elements denoted by the same reference numerals as shown in FIG. 1 and described in connection with the first embodiment, except for the stimuli-responsive substance 3'. The stimuli-responsive substance 3' can be identical with or similar to the stimuli-responsive substance 3' described in connection with the third embodiment. Therefore, these elements are not described in detail again.

The catheter according to the fourth embodiment is based on that according to the third embodiment. That is, it can comprise at least one tour or inflow pipe 5' and at least one return or outflow pipe 5" in addition to the above components. Further, the container 3 may comprise at least one flexible portion 6 such as e.g. a flexible wall. These components can be identical with or similar to the elements denoted by the same reference numerals as shown in FIGS. 4(*a*) and 4(*b*) and described in connection with the third embodiment. Therefore, they are not described in detail again.

The catheter according to the fourth embodiment may additionally comprise at least one portion 5''' extending around the supply unit 2 and/or the element 2'. It may interconnect the at least one inflow pipe 5' and the at least one outflow pipe 5" and form a cooling system with the same. The at least one portion 5''' can be c-shaped, annular or have some other shape. The cooling system may be used to cool the catheter tip and in turn the material 4. It can be controlled similar as the cooling system of the third embodiment.

The catheter according to the fourth embodiment enables to perform an ablation in the same manner as described in connection with the first embodiment. When the temperature of the material 4 is below a certain (upper) threshold temperature, the at least one flexible portion 6 of the container 3 may be pushed by means of the stimuli-responsive substance 3' in order to obstruct or partially obstruct the flow of cooling fluid in the cooling system. More specifically, the flow of the cooling fluid in the at least one portion 5''' can be obstructed or partially obstructed by the pushed at least one flexible portion 6 of the container 3. Thus, it may be prevented that cooling fluid flows through the cooling system, or only a reduced amount of the cooling fluid can be allowed to flow. FIG. 6(*a*) illustrates the state where the temperature of the material 4 is below the upper threshold temperature and, therefore, the cooling system is closed or at least partially closed.

Once the temperature of the material 4 increases above the upper threshold temperature, the at least one flexible portion 6 may not be pushed and retract, letting the cooling fluid or an increased amount of the cooling fluid flow through the cooling system, i.e. the at least one portion 5'''. As a result, the temperature of the catheter tip and consequently that of the material 4 can be reduced. FIG. 6(*b*) illustrates the state where the temperature of the material 4 is above the upper threshold temperature and, therefore, the cooling system is open.

As described above, the stimuli-responsive substance 3' may change its state from a first state to a second state if the temperature of the material 4 increases above the upper threshold temperature due to the ablation energy, so that the temperature of the material 4 does not increase above a temperature limit of e.g. 70° C. and detrimental effects due to an overheating are prevented. On the other hand, the stimuli-responsive substance 3' can change its state back from the second state to the first state if the temperature of the material 4 decreases below a lower threshold temperature that may be identical with the upper threshold temperature or differ from the same. Thus, the temperature of the material 4 does not decrease below a further temperature limit.

In this manner, the temperature of the material 4 can be kept in a certain interval, without the risk of exceeding a temperature threshold or limit. Thus, detrimental effects resulting from an overheating may be avoided.

In the catheter according to the fourth embodiment, the cooling system and the supply unit 2 and/or element 2' are coaxially located. A path from the distal end of the supply unit 2 to the ablation or treatment site 4' does not intersect the cooling system and/or the stimuli-responsive substance 3'. Cooling fluid can flow around the supply unit 2 and/or the element 2', without crossing a path of the ablation energy. Hence, it is not necessary that the cooling fluid and the stimuli-responsive substance 3' are transparent to the ablation energy, e.g. optically transparent in case of using laser energy (light).

While only a single inflow pipe 5' and a single outflow pipe 5" are shown in FIGS. 6(*a*) and 6(*b*), multiple inflow pipes and/or multiple outflow pipes may be present. Further, the container 3 can have an annular form and extend around the supply unit 2 and the element 2' as illustrated in FIGS. 6(*a*) and 6(*b*). However, there may also be a plurality of containers 3 that can be located e.g. equidistant from each other and around the supply unit 2 and the element 2', and may respectively comprise a stimuli-responsive substance 3' capable of changing its geometrical properties and at least one flexible portion 6 pushed by the stimuli-responsive substance 3'. Moreover, a plurality of portions 5''' extending around the supply unit 2 and/or the element 2' as well as corresponding containers 3 respectively comprising a stimuli-responsive substance 3' and at least one flexible portion 6 pushed by the same are possible.

While FIGS. 6(*a*) and 6(*b*) show a specific arrangement, other variants as described in connection with e.g. the first and third embodiments are feasible. Further, the same considerations with respect to the distance between the distal end of the supply unit 2 and the treatment area 4' as for the first embodiment apply.

As described above, a safe ablation catheter based on a catheter tip cooling system can be provided. The stimuli-responsive substance 3' may change its geometrical properties in order to control the cooling system. In this way, the temperature of the material 4 can be regulated by cooling it with the catheter tip in turn cooled by the cooling system. Thus, an overheating of the material 4 and detrimental effects resulting from such overheating may be prevented.

Figure 7:
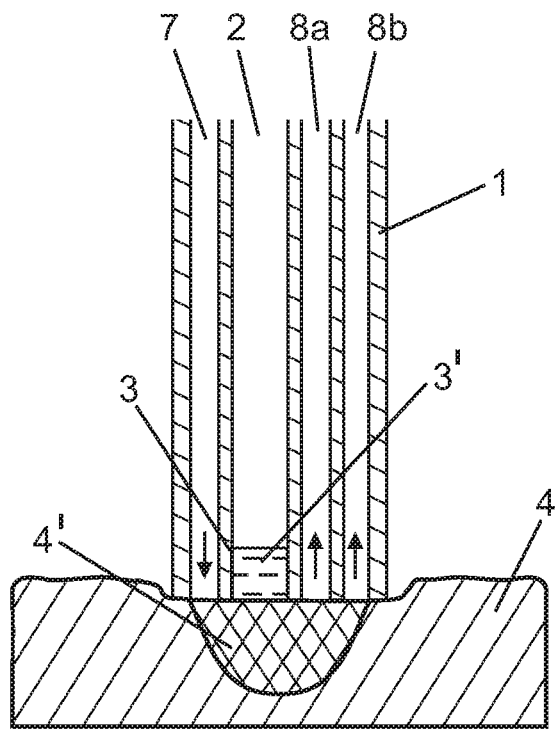
FIG. 7 shows a schematic diagram illustrating an exemplary device according to a fifth embodiment.

FIG. 7 shows a schematic diagram illustrating an exemplary device according to a fifth embodiment. It depicts a schematic cross section of a catheter that may be applied to thermally treat material. More specifically, it depicts a cross section of the distal end of the catheter, i.e. the catheter tip.

The catheter can comprise a catheter housing 1, a supply unit 2 such as e.g. an (optical) fiber or ablation fiber, an (optional) element 2' covering the distal end of the supply unit 2, and a container 3 comprising a stimuli-responsive material or substance 3'. These components as well as a target material 4 and an area or site 4' at the material 4 may be identical with or similar to the elements denoted by the same reference numerals as shown in FIG. 1 and described in connection with the first embodiment. Therefore, they are not described in detail again.

In addition to the above components, the catheter according to the fifth embodiment can comprise at least one illumination unit 7 such as e.g. an (optical) fiber and at least one collection or reception unit 8*a*, 8*b* such as e.g. an (optical) fiber. These additional components enable to obtain information about the status or state of the material 4 as described in more detail below. They can be in contact with the material 4. In this way, as much reflected light as possible (i.e. as many back-reflected photons as possible) may be collected.

As described above, the supply unit 2 can supply laser energy to the treatment site 4'. That is, the supply unit 2 may be used to transport laser light from a laser source to the material 4. High-power laser light can be applied to achieve a desired ablation. In order to protect the material 4 from overheating, the stimuli-responsive substance 3' such as e.g.

a temperature-sensitive gel may be placed between the distal end of the supply unit 2 and the material 4.

The at least one illumination unit 7 and the at least one reception unit 8a, 8b can form a measuring system for measuring reflected light. They may be used to follow the size, quality and growing of the treatment site 4' that can be considered to be some kind of lesion in case of treating tissue. Through the at least one illumination unit 7, the material 4 may be illuminated by illumination light. A power of the illumination light can be quite small. In particular, it may be much smaller than a power of ablation laser light. Reflected or backscattered light can be collected or received by the at least one reception unit 8a, 8b. Information obtained by means of the at least one reception unit 8a, 8b includes, but is not limited to, information about the status (e.g. size, quality, etc.) of the treated material. Such information may be used to determine the time and power of the ablation energy supplied through the supply unit 2. It may be feed back to a control unit such as e.g. electronics for controlling a source of the ablation energy. Consequently, e.g. parameters of a lesion formation (e.g. size, quality, speed of lesion formation, etc.) can be controlled.

By using the measurements performed by the measuring system, parameters of a thermal process, such as e.g. temperature and absorbed light in the material 4, may be determined. Based on such estimations, a power of the ablation energy can be adopted in real time in order to optimize an effect of a thermal treatment.

While only a single illumination unit 7 and two reception units 8a, 8b are shown in FIG. 7, multiple illumination units and/or more than two reception units may be present. For example, various reception units positioned at different distances with respect to the at least one illumination unit 7 can be used to measure different layers of the material 4 located at different depths of the same.

While FIG. 7 shows a specific arrangement, other variants as described in connection with e.g. the first embodiment are feasible. Further, the same considerations with respect to the distance between the distal end of the supply unit 2 and the treatment area 4' as for the first embodiment apply.

As described above, a safe ablation catheter based on a stimuli-responsive substance and a measuring system may be provided. A level of energy deposited into thermally treated material can be regulated by means of the stimuli-responsive substance. An ablation procedure performed by the catheter may be controlled in real time by means of information obtained by the measuring system. Thus, an overheating of the material and detrimental effects resulting from such overheating can be prevented, and an ablation procedure may be controlled in real time. Further, a therapist or other operator of the ablation procedure can be provided with information about the same.

Figure 8:
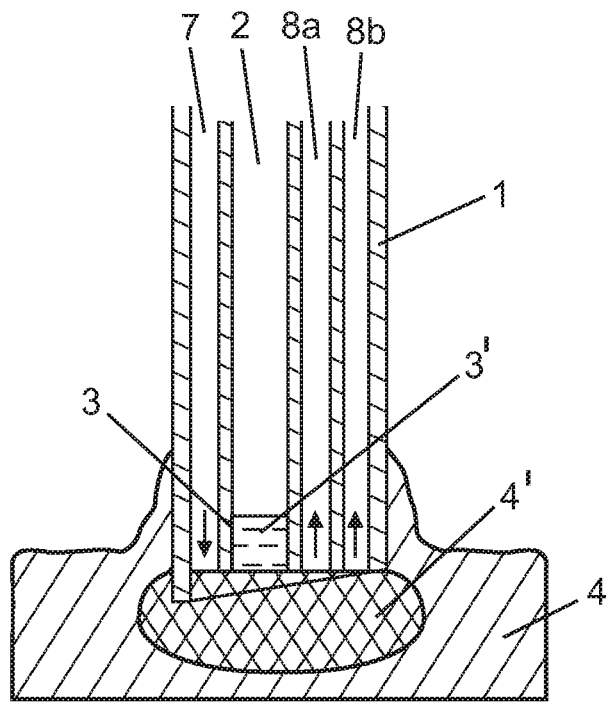
FIG. 8 shows a schematic diagram illustrating an exemplary device according to a sixth embodiment.

FIG. 8 shows a schematic diagram illustrating an exemplary device according to a sixth embodiment. It depicts a schematic cross section of a needle that may be applied to thermally treat material. More specifically, it depicts a cross section of the distal end of the needle, i.e. the needle tip.

The needle can comprise a needle housing 1, a supply unit 2 such as e.g. an (optical) fiber or ablation fiber, an (optional) element 2' covering the distal end of the supply unit 2, and a container 3 comprising a stimuli-responsive material or substance 3', wherein the element 2' is not shown in FIG. 8. These components as well as a target material 4 and an area or site 4' at the material 4 may be identical with or similar to the elements denoted by the same reference numerals as shown in FIG. 1 and described in connection with the first embodiment. Therefore, they are not described in detail again.

The needle according to the sixth embodiment is based on the catheter according to the fifth embodiment. In addition to the above components, it can comprise at least one illumination unit 7 such as e.g. an (optical) fiber and at least one reception unit 8a, 8b such as e.g. an (optical) fiber. These components may be identical with or similar to the components denoted by the same reference numerals as shown in FIG. 7 and described in connection with the fifth embodiment. Therefore, they are not described in detail again.

The needle according to the sixth embodiment enables to perform an ablation in the same manner as described in connection with the first and fifth embodiments, except for the ablation or treatment site 4' not being placed at the surface of the material 4 but rather located inside of the material 4 as described in connection with the second embodiment. A level of energy deposited into the material 4 can be regulated by means of the stimuli-responsive substance 3'. A power of the ablation energy may be adopted in real time in order to optimize an effect of a thermal treatment.

While FIG. 8 shows a specific arrangement, other variants as described in connection with e.g. the first, second and fifth embodiments are feasible. Further, the same considerations with respect to the distance between the distal end of the supply unit 2 and the treatment area 4' as for the first embodiment apply.

As described above, a safe ablation needle based on a stimuli-responsive substance and a measuring system can be provided. The needle may be called an intelligent needle. A level of energy deposited into thermally treated material can be regulated by means of the stimuli-responsive substance. An ablation procedure performed by the needle may be controlled in real time by means of information obtained by the measuring system. Thus, an overheating of the material and detrimental effects resulting from such overheating can be prevented, and an ablation procedure may be controlled in real time. Further, a therapist or other operator of the ablation procedure can be provided with information about the same.

Figure 9:
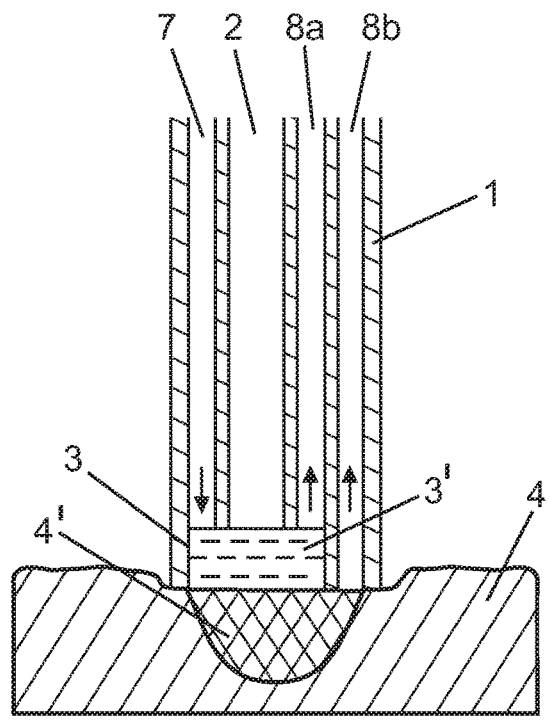
FIG. 9 shows a schematic diagram illustrating an exemplary device according to a seventh embodiment.

FIG. 9 shows a schematic diagram illustrating an exemplary device according to a seventh embodiment. It depicts a schematic cross section of a catheter that may be applied to thermally treat material. More specifically, it depicts a cross section of the distal end of the catheter, i.e. the catheter tip.

The catheter can comprise a catheter housing 1, a supply unit 2 such as e.g. an (optical) fiber or ablation fiber, an (optional) element 2' covering the distal end of the supply unit 2, and a container 3 comprising a stimuli-responsive material or substance 3'. These components as well as a target material 4 and an area or site 4' at the material 4 may be identical with or similar to the elements denoted by the same reference numerals as shown in FIG. 1 and described in connection with the first embodiment. Therefore, they are not described in detail again.

The catheter according to the seventh embodiment is based on that according to the fifth embodiment. It differs from the latter in that the at least one illumination unit 7 and at least one of the at least one reception unit 8a, 8b (e.g. the reception unit 8a as shown in FIG. 9) can be in contact with the container 3 comprising the stimuli-responsive substance 3' or even with the stimuli-responsive substance 3' itself.

When the temperature of the material 4 rises, the temperature of the stimuli-responsive substance 3' may also rise.

As a result, optical characteristics of the stimuli-responsive substance 3' can change. Consequently, the intensity of reflected or backscattered light may also change. This change can be measured by using the at least one illumination unit 7 and the at least one reception unit 8a, 8b. A first reception unit 8a may receive reflected light passing through the stimuli-responsive substance 3', and a second reception unit 8b can receive reflected light not passing through the stimuli-responsive substance 3'. Thus, there may be a direct feedback on a behavior of the stimuli-responsive substance 3' such as a temperature-sensitive material and a development of the treatment site 4' such as a lesion at the same time, while the material 4 can be protected from being overheated.

The catheter according to the seventh embodiment enables to perform an ablation in a similar manner as described in connection with the first and fifth embodiments. A level of energy deposited into the material 4 can be regulated by means of the stimuli-responsive substance 3'. A power of the ablation energy may be adopted in real time in order to optimize an effect of a thermal treatment. In addition, a direct feedback on the behavior of the stimuli-responsive substance 3' and the development of the treatment site 4' may be provided at the same time.

While FIG. 9 shows a specific arrangement, other variants as described in connection with e.g. the first and fifth embodiments are feasible. Further, the same considerations with respect to the distance between the distal end of the supply unit 2 and the treatment area 4' as for the first embodiment apply.

As described above, a safe ablation catheter based on a stimuli-responsive substance and a measuring system can be provided. A level of energy deposited into thermally treated material may be regulated by means of the stimuli-responsive substance. An ablation procedure performed by the catheter can be controlled by means of information obtained by the measuring system. In addition, a direct feedback on the behavior of the stimuli-responsive substance and the development of a treatment site at the material may be provided at the same time. Thus, an overheating of the material and detrimental effects resulting from such overheating can be prevented, and an improved control of an ablation procedure in real time may be enabled. Further, a therapist or other operator of the ablation procedure can be provided with information about the same. Hence, a safe and controllable ablation catheter may be provided.

Figure 10:
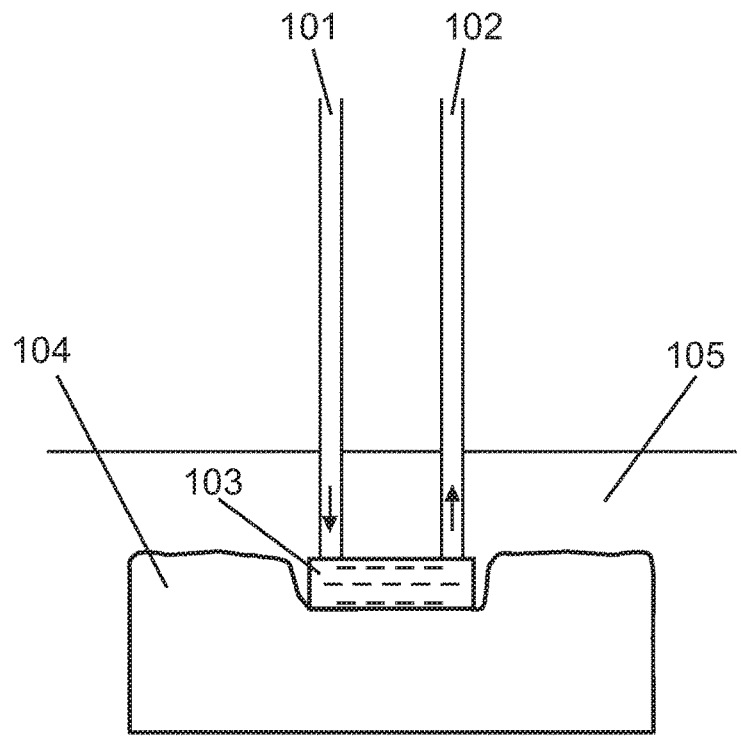
FIG. 10 shows a schematic diagram illustrating an experimental arrangement used to perform a proof of principle for the fifth to seventh embodiments.

FIG. 10 shows a schematic diagram illustrating an experimental arrangement used to perform a proof of principle for the fifth to seventh embodiments. The arrangement can comprise an illumination fiber 101, a reception fiber 102, a stimuli-responsive substance 103 such as e.g. a temperature-sensitive hydrogel, a material 104 such as e.g. a tissue, and water 105.

For the experiment, a temperature-sensitive hydrogel was used as the stimuli-responsive substance 103. A reaction mixture consisting of 25 wt % deionized water, 25 wt % methanol, 48.9 wt % NIPAAm+0.1 wt % diethyleneglycoldiacrylate+1 wt % IRG 2959 photo-initiator, which had been polymerized by applying ultraviolet (UV) radiation (100 mW/cm$^2$) for about 90 seconds, was employed. The distance between the illumination fiber 101 and the reception fiber 102 was 1.5 mm.

During the experiment, the material 104 was illuminated by light supplied by the illumination fiber 101, and reflected or backscattered light was received by the reception fiber 102 to measure an intensity of the reflected light. The spectrum of the reflected light passing through the stimuli-responsive substance 103 was measured at various temperatures of the stimuli-responsive substance 103.

Figure 11:
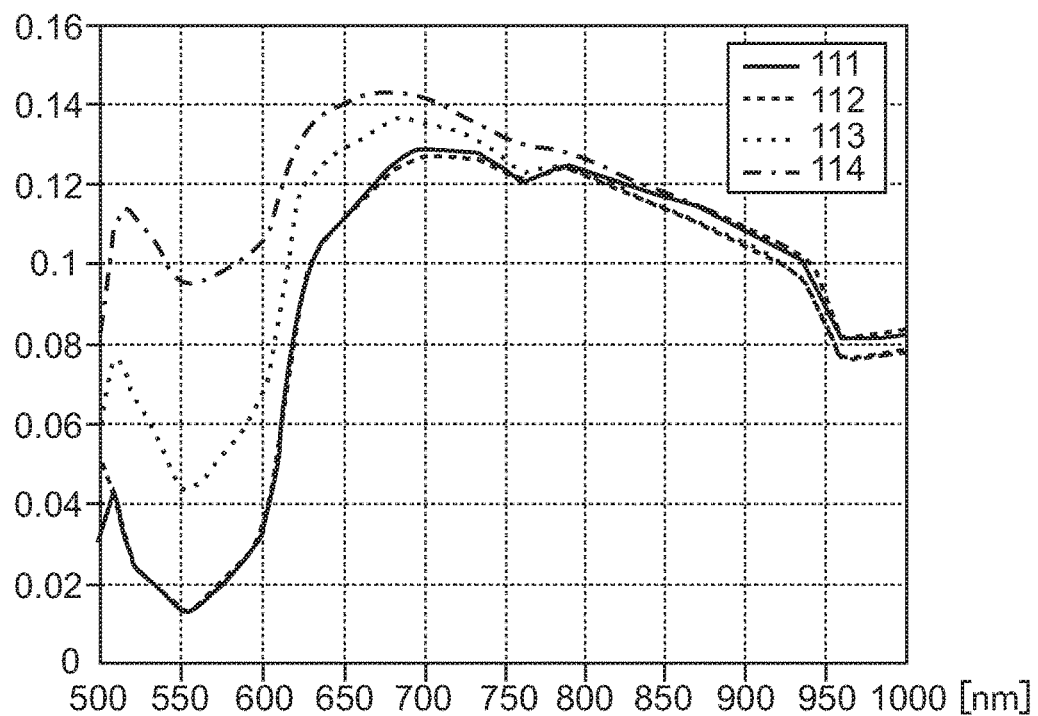
FIG. 11 shows a schematic diagram illustrating results obtained with the experimental arrangement depicted in FIG. 10.

FIG. 11 shows a schematic diagram illustrating results obtained with the experimental arrangement depicted in FIG. 10. On the horizontal axis the wavelength of the illumination light supplied by the illumination fiber 101 is indicated in nm, and on the vertical axis the intensity of the reflected light received by the reception fiber 102 with respect to the reference is indicated as a function of the temperature of the stimuli-responsive substance 103. Reference values 111 to 114 denote curves for temperatures of 22° C., 30° C., 37° C. and 43° C., respectively. As illustrated in FIG. 11, the higher the temperature is, the greater the respective intensity is in general. For example, the path of the curve 114 for a temperature of 43° C. is at a higher level than that of the curve 113 for a temperature of 37° C.

Figure 12:
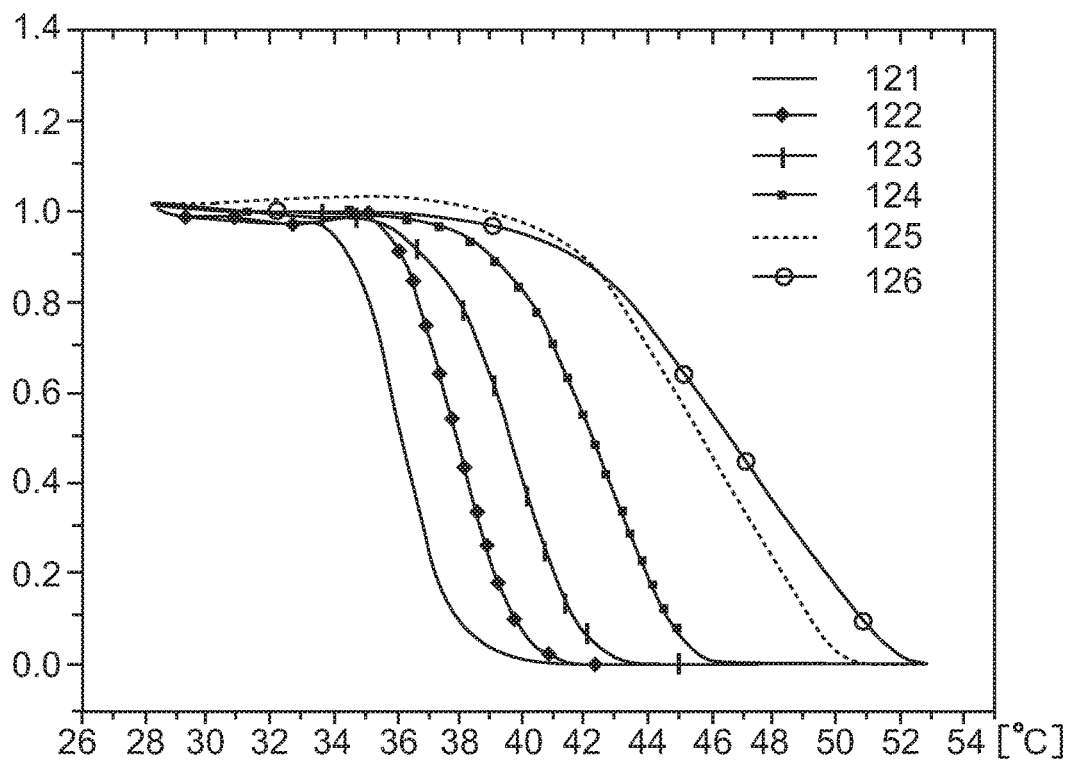
FIG. 12 shows a schematic diagram illustrating a transmission of a temperature-sensitive hydrogel versus the temperature for various consistencies of the temperature-sensitive hydrogel.

FIG. 12 shows a schematic diagram illustrating a transmission of a temperature-sensitive hydrogel versus the temperature for various consistencies of the temperature-sensitive hydrogel. On the horizontal axis the temperature of the hydrogel is indicated in ° C., and on the vertical axis the transmission (transmittance) of the hydrogel is indicated as a function of the molar ratio in the hydrogel. Reference values 121 to 126 denote curves for molar ratios of 2%, 3%, 5%, 6%, 8% and 9%, respectively, of poly ethylene glycol diacrylate (PEGA) (comonomer) with respect to N-isopropylacrylamide (NIPA) in the hydrogel. As illustrated, the LCST could be varied between 36° C. and 47° C. by increasing the ratio of PEGA.

The optical transition of temperature-sensitive hydrogel samples is illustrated in FIG. 12, where the one used in the proof of principle as performed with the experimental arrangement shown in FIG. 10 is denoted by the reference numeral 124. The spectroscopic measurements presented in FIG. 11 are in good agreement with the optical transition characteristic of the hydrogel sample shown in FIG. 12.

Figures 13A, 13B:
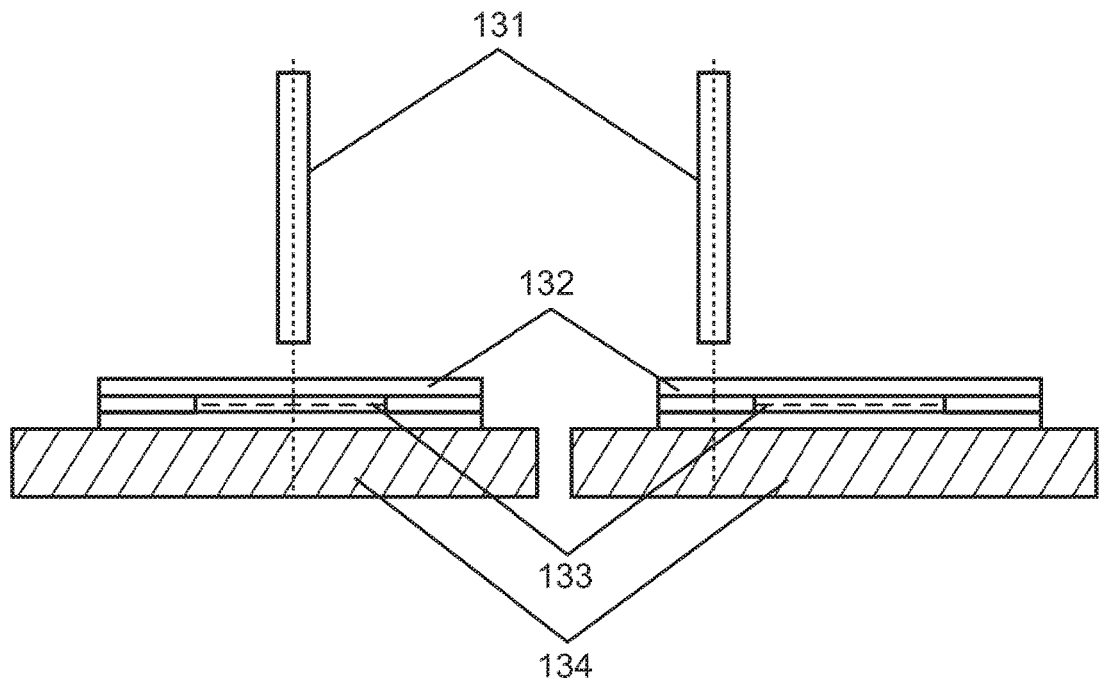
FIGS. 13(a) and 13(b) show schematic diagrams illustrating experimental arrangements used to compare results of ablating through the temperature-sensitive hydrogel and ablating only through glass sheets.

FIGS. 13(a) and 13(b) show schematic diagrams illustrating experimental arrangements used to compare results of ablating through the temperature-sensitive hydrogel and ablating only through glass sheets. The arrangements can respectively comprise an optical fiber 131 for ablation, glass sheets 132, a hydrogel 133, and a material 134.

For the performed experiment, the thickness of the hydrogel 133 was 0.5 mm, and the material 134 was pig heart tissue. The results of ablating through both of the glass sheets 132 and the hydrogel 133 versus ablating only through the glass sheets 132 were compared for the same ablation parameters, the same tissue, the same distance from the tissue and the same temperature of the bath. The ablation site was practically shifted by a couple of millimeters. FIG. 13(a) illustrates the situation when ablating through the hydrogel 133. FIG. 13(b) illustrates the situation when ablating only through the glass sheets 134. The pig heart tissue was placed under the same glass sheets. Therefore, their effect could be neglected when comparing lesions resulting from the ablation.

When the ablation was occurring through the hydrogel 133, which above a certain threshold temperature scatters the ablation light and, thus, blocks out a further heating of the tissue, the lesion did not turn brown like in the case of ablating only through the glass sheets 134. Thus, it could be shown that the hydrogel 133 enables a temperature protection. It could be observed that the lesion was not as big in the first case, which is attributed to the conductive heating of the tissue, since the highest temperature reached in the lesion is controlled by the hydrogel. The ablation was performed with an optical power of 3.1 W at a wavelength of 967 nm.

Figure 14:
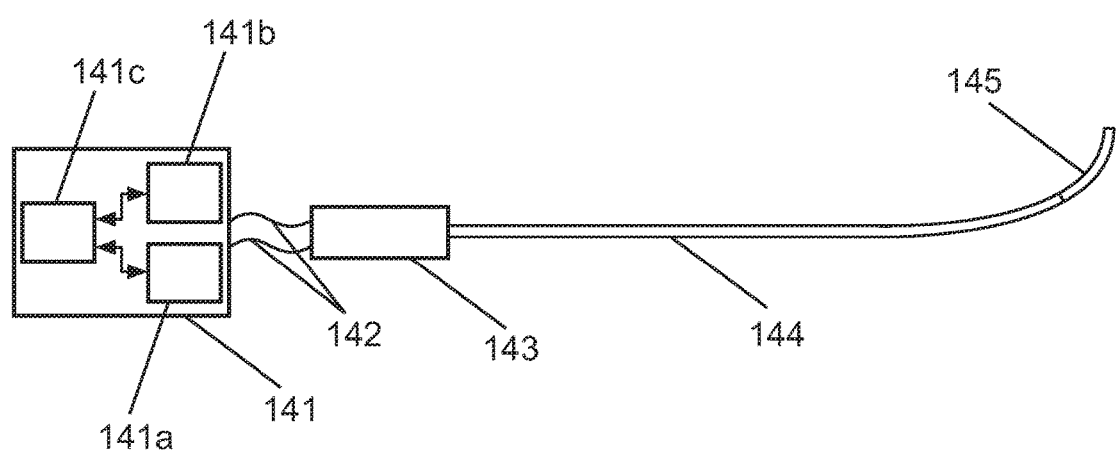
FIG. 14 shows a schematic diagram illustrating a system according to the embodiments.

FIG. 14 shows a schematic diagram illustrating a system according to the embodiments. The system such as e.g. an ablation catheter system can comprise a unit 141 including energy source(s) 141a such as e.g. at least one laser ablation energy source, illumination source(s) 141b for providing illumination light, and all needed electronics 141c such as e.g. a control unit for regulating the energy source(s) 141a. It may further comprise one or more connecting cables 142, a handler 143, and a device such as e.g. a catheter 144 including a distal/treatment portion 145 such as e.g. a catheter tip.

Ablation energy generated by the energy source(s) 141a and illumination light generated by the illumination source (s) 141b can be transported to the device 144. At the distal/treatment portion 145 of the device 144 the ablation energy may be supplied to material such as e.g. tissue. Then, the material can be heated locally and, consequently, an ablation procedure may be performed. Further, the illumination light can be used for measuring purposes. The handler 143 enables to manipulate with the device 144.

The device 144 may correspond to any one of the devices according to the first to seventh embodiments. If it corresponds to one of the devices according to the fifth to seventh embodiments, it can obtain information about a state of the material by means of the measuring system comprising the at least one illumination unit 7 and the at least one reception unit 8a, 8b. In this case, the control unit 141c may control or regulate the energy source(s) 141a based on the obtained information.

Figure 15:
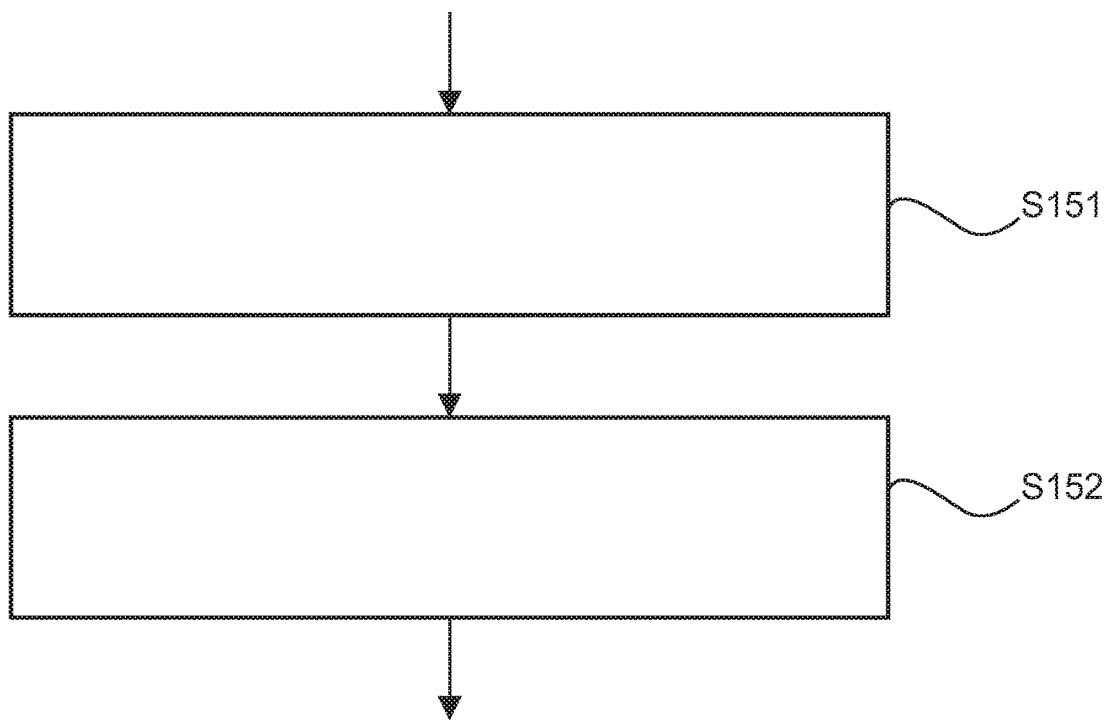
FIG. 15 shows a flowchart illustrating basic steps of an exemplary method according to the embodiments.

FIG. 15 shows a flowchart illustrating basic steps of an exemplary method according to the embodiments. The method can comprise a step S151 of supplying ablation energy to a material. Further, it may comprise a step S152 of changing a state of a stimuli-responsive substance from a first state to a second state if a temperature of the material increases above an upper threshold temperature due to the ablation energy, so that the temperature of the material does not increase above a temperature limit.

Figure 16:
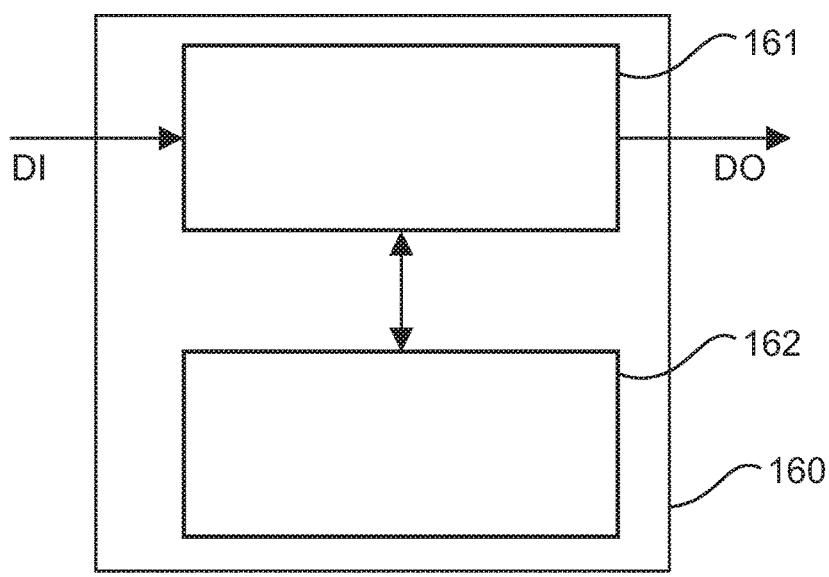
FIG. 16 shows an example of a software-based implementation of the embodiments.

FIG. 16 shows an example of a software-based implementation of the embodiments. Here, a device 160 comprises a processing unit (PU) 161, which may be provided on a single chip or a chip module and which may be any processor or computer device with a control unit that performs control based on software routines of a control program stored in a memory (MEM) 162. Program code instructions are fetched from the MEM 162 and loaded into the control unit of the PU 161 in order to perform processing steps such as those described in connection with FIG. 15. The processing steps can be performed on the basis of input data DI and may generate output data DO.

In summary, the present invention relates to a device comprising a supply unit 2 for supplying ablation energy to a material 4, and a stimuli-responsive substance 3' for controlling a level of the ablation energy deposited into the material 4. The device allows to limit a temperature of the material 4, so that risks associated to ablation at too high temperatures can be eliminated. The device may comprise at least one illumination unit 7 for illuminating the material 4, and at least one reception unit 8a, 8b for receiving reflected light in order to obtain information about a state of the material 4. The obtained information can be used to regulate the supplied ablation energy.

While the present invention has been illustrated and described in detail in the drawings and foregoing description, such illustration and description are to be considered illustrative or exemplary and not restrictive. The invention is not limited to the disclosed embodiments. For example, the mechanisms for actively controlling a cooling system as described in connection with the third and fourth embodiments can also be used to control an irrigation system. That is, a stimuli-responsive substance configured to change its geometrical properties may be employed to control such irrigation system. In case that the irrigation system is a closed one, it may be equivalent to the cooling system. In case it is an open irrigation system, irrigation fluid can be supplied and/or drained via one or more openings at a tip of a catheter comprising the irrigation system. The irrigation system may be used to perform an irrigation in order to prevent an overheating or for other purposes.

Thus, the same regulatory system based on one or more stimuli-responsive substances can be applied for irrigation catheters, so that the amount of irrigation fluid used during the ablation does not become very significant. Irrigation catheters may have alternative energy sources other than a laser energy source, such as e.g. radio frequency (RF) or high intensity focused ultrasound (HIFU) energy sources.

If an irrigation fluid overload occurs during e.g. an atrial fibrillation (AF) treatment by means of an irrigation catheter, side effects such as dyspnea, chest tightness, wheezing, lung crackles or combinations of them can be caused. In this respect, the amount of irrigation fluid to be released at the tip of the catheter in the blood stream may depend strongly on the temperature of the ablation site. By using stimuli-responsive substances, the released amount of irrigation fluid can be suitably regulated. Thus, an amount of irrigation fluid used during an ablation may not become very significant. Hence, an irrigation fluid overload causing side effects can be avoided.

While exemplary embodiments have been described, the present invention is not limited to these embodiments. For example, features of multiple embodiments may be combined. For instance, a catheter or a needle can comprise a first stimuli-responsive substance capable of changing its optical properties as described e.g. in connection with the first embodiment, and further comprise a cooling system and a second stimuli-responsive substance capable of changing its geometrical properties as described e.g. in connection with the third and fourth embodiments. The first stimuli-responsive substance may be used to regulate a level of energy deposited into material during an ablation procedure, and the second stimuli-responsive substance can be used to control the cooling system. In this way, an efficient and redundant mechanism for preventing an overheating of the material and detrimental effects resulting from such overheating may be provided.

The devices and procedures described above can be applied wherever a thermal treatment may be used. For example, they can be employed for a heart tissue ablation applicable for various diseases (e.g. an endocardial and epicardial thermal therapy for a treatment of e.g. an atrial fibrillation), a prostate treatment, in oncology for tumor ablation, a treatment of kidney, bladder and other cancerous tissue, etc.

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program capable of controlling a processor to perform the claimed features can be stored/distributed on a suitable medium, such as an optical storage medium or a solid-state medium supplied together with or as part of other hardware, but may also be distributed in other forms, such as via the Internet or other wired or wireless telecommunication systems. It can be used in conjunction with a new system, but may also be applied when updating or upgrading existing systems in order to enable them to perform the claimed features.

A computer program product for a computer can comprise software code portions for performing e.g. processing steps such as those described in connection with FIG. 15 when the computer program product is run on the computer. The computer program product may further comprise a computer-readable medium on which the software code portions are stored, such as e.g. an optical storage medium or a solid-state medium.

Any reference signs in the claims should not be construed as limiting the scope thereof.

The invention claimed is:

1. Device comprising:
    a supply unit configured to supply ablation energy to a material; and
    a container comprising a stimuli-responsive substance adjacent the material;
    wherein said stimuli-responsive substance is configured to change its state from a first state to a second state if a temperature of said material increases above an upper threshold temperature due to at least a portion of said ablation energy passing through said stimuli-responsive substance into the material, so that said temperature of said material does not increase above a temperature limit
    a cooling system configured to cool said device,
    wherein said stimuli-responsive substance is configured to change its geometrical properties in order to control said cooling system.

2. Device according to claim 1, wherein said stimuli-responsive substance is configured to change its state back from said second state to said first state if said temperature of said material decreases below a lower threshold temperature.

3. Device according to claim 1, wherein said stimuli-responsive substance is a temperature-sensitive gel.

4. Device according to claim 1, wherein said stimuli-responsive substance is configured to change its optical properties from being transparent to being scattering and/or absorbing if said temperature of said material increases above said upper threshold temperature.

5. Device according to claim 1, wherein said cooling system comprises at least one inflow pipe and at least one outflow pipe, and wherein said container comprises at least one flexible portion configured to disable a connection between said at least one inflow pipe and said at least one outflow pipe at least partially if said temperature of said material is equal to or below said upper threshold temperature and to enable said connection if said temperature of said material increases above said upper threshold temperature.

6. Device according to claim 1, wherein said cooling system comprises at least one portion configured to extend around said supply unit.

7. Device according to claim 1, wherein said supply unit is a fiber and said ablation energy is laser energy.

8. Device according to claim 1, wherein said device is a catheter or a needle.

9. Method comprising:
    supplying ablation energy to a material;
    changing a state of a stimuli-responsive substance adjacent the material from a first state to a second state if a temperature of said material increases above an upper threshold temperature due to at least a portion of said ablation energy passing through said stimuli-responsive substance into the material, so that said temperature of said material does not increase above a temperature limit; and
    controlling a cooling system for cooling a device supplying the ablation energy, the stimuli-responsive substance being configured to change its geometrical properties in order to control the cooling system.

* * * * *